US012718949B2

(12) United States Patent
Marquet et al.

(10) Patent No.: US 12,718,949 B2
(45) Date of Patent: Aug. 25, 2026

(54) COMPUTER-IMPLEMENTED DIAGNOSTIC METHOD FOR DETERMINING THE CLINICAL INTERPRETATION OF RENAL GRAFT ALTERATIONS

(71) Applicants: INSTITUT NATIONAL DE LA SANTÉ ET DE LA RECHERCHE MÉDICALE, Paris (FR); KATHOLIEKE UNIVERSITEIT LEUVEN, Leuven (BE); CENTRE HOSPITALIER ET UNIVERSITAIRE DE LIMOGES, Limoges (FR); UNIVERSITE DE LIMOGES, Limoges (FR)

(72) Inventors: Pierre Marquet, Limoges (FR); Marc Labriffe, Limoges (FR); Dany Anglicheau, Paris (FR); Wilfried Gwinner, Hannover (DE); Maarten Naesens, Leuven (BE)

(73) Assignees: INSERM (INSTITUT NATIONAL DE LA SANTE ET DE LA RECHERCHE MEDICALE), paris (FR); KATHOLIEKE UNIVERSITEIT LEUVEN, Leuven (BE); CENTRE HOSPITALIER ET UNIVERSITAIRE DE LIMOGES, Limoges (FR); UNIVERSITE DE LIMOGES, Limoges (FR)

( * ) Notice: Subject to any disclaimer, the term of this patent is extended or adjusted under 35 U.S.C. 154(b) by 344 days.

(21) Appl. No.: 18/557,357

(22) PCT Filed: Apr. 28, 2022

(86) PCT No.: PCT/EP2022/061297
§ 371 (c)(1),
(2) Date: Oct. 26, 2023

(87) PCT Pub. No.: WO2022/229303
PCT Pub. Date: Nov. 3, 2022

(65) Prior Publication Data

US 2024/0212850 A1 Jun. 27, 2024

(30) Foreign Application Priority Data

Apr. 29, 2021 (EP) .................................... 21305557

(51) Int. Cl.
*G16H 50/20* (2018.01)
*A61B 5/00* (2006.01)

(52) U.S. Cl.
CPC ........... *G16H 50/20* (2018.01); *A61B 5/4848* (2013.01)

(58) Field of Classification Search
CPC .............................. G16H 50/20; A61B 5/4848
See application file for complete search history.

(56) References Cited

U.S. PATENT DOCUMENTS 8,346,349 B2 * 1/2013 Guttag ............... A61B 5/02405 600/509
9,752,191 B2 * 9/2017 Salomon ............. C12Q 1/6883
(Continued)

FOREIGN PATENT DOCUMENTS

EP 3 712 898 A1 9/2020

OTHER PUBLICATIONS

González, 2020, Elsevier, pp. 205-237.*
(Continued)

*Primary Examiner* — Michael I Ezewoko
(74) *Attorney, Agent, or Firm* — WCF IP

(57) ABSTRACT

The invention relates to a computer-implemented diagnostic method learning for determining clinical interpretation of
(Continued)

Figure 1:
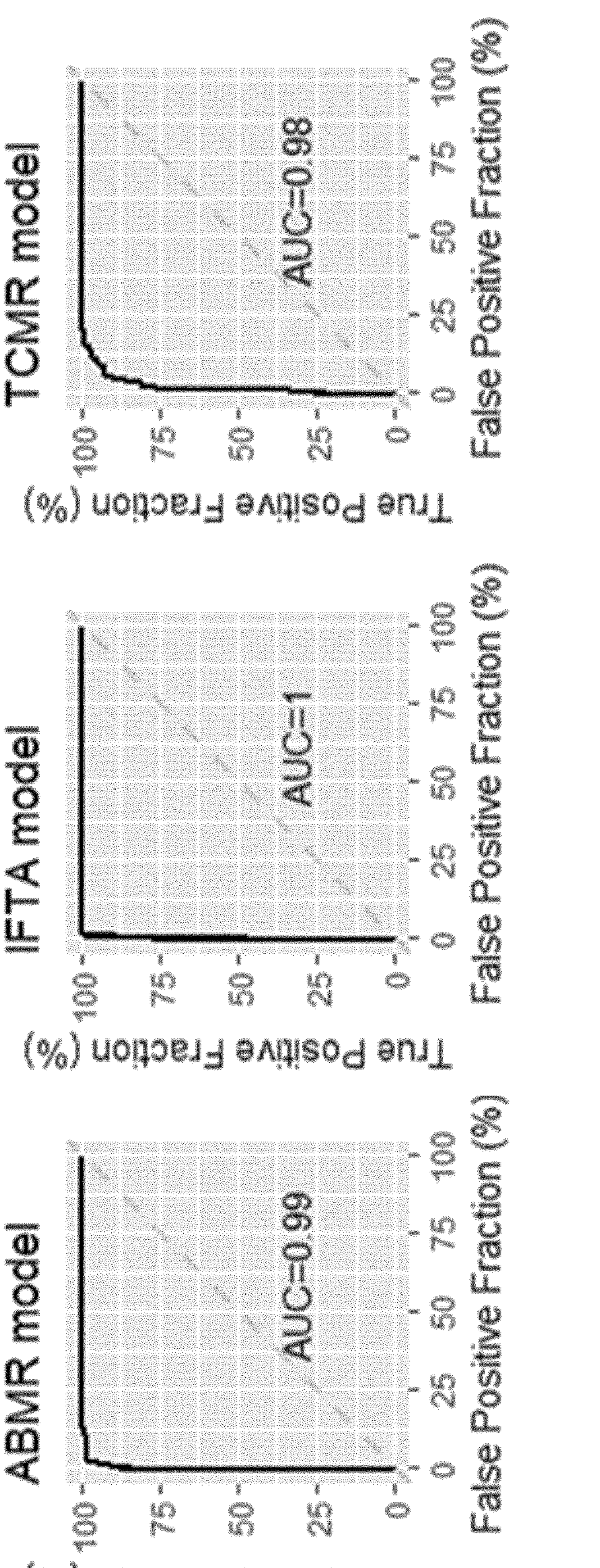

renal graft alterations by applying a trained machine-learning model and a method for training a model for determining clinical categories based on renal transplant lesions, clinical signs and routine laboratory test results.

17 Claims, 6 Drawing Sheets

(56) References Cited

U.S. PATENT DOCUMENTS 9,816,985 B2 * 11/2017 Murphy .................. A61P 13/12
11,645,753 B2 * 5/2023 Madabhushi ......... G06T 7/0014 382/128
11,657,505 B1 * 5/2023 Beck ...................... G16H 50/30 382/128
11,657,921 B2 * 5/2023 Zimmerman ........ G06N 3/0495 600/301
11,674,181 B2 * 6/2023 Murphy ............... C12Q 1/6883 424/134.1
11,754,824 B2 * 9/2023 Ince ......................... G06N 3/08 348/79
11,821,037 B2 * 11/2023 Salomon .............. C12Q 1/6883
11,865,175 B1 * 1/2024 Jordan .................... A61P 37/06
11,978,208 B2 * 5/2024 Goto ..................... G06T 7/0016
12,073,948 B1 * 8/2024 Beck ...................... G16H 50/30
12,159,403 B2 * 12/2024 Madabhushi ........ A61B 5/7267
12,209,284 B2 * 1/2025 Salomon .............. C12Q 1/6883
12,234,509 B2 * 2/2025 Moshkevich ........ C12Q 1/6851
12,340,560 B2 * 6/2025 Bai ...................... G06V 10/764
2003/0187584 A1 * 10/2003 Harris .................... G16H 10/40 702/19
2003/0232867 A1 * 12/2003 Kobayashi ............. A61K 31/42 514/378
2004/0059697 A1 * 3/2004 Forman ................. G06F 18/211 706/46
2005/0262031 A1 * 11/2005 Saidi ....................... G16Z 99/00 600/407
2006/0211725 A1 * 9/2006 Kobayashi ......... A61K 31/4523 514/378
2007/0009517 A1 * 1/2007 De Boer ................ A61K 31/00 514/233.2
2009/0093010 A1 * 4/2009 Nickerson .......... G01N 33/6893 435/23
2010/0104581 A1 * 4/2010 Brouard .................... A61P 1/00 435/6.1
2011/0104700 A1 * 5/2011 Halloran ............ G01N 33/5088 435/6.1
2012/0178642 A1 * 7/2012 Salomon .............. C12Q 1/6883 506/9
2015/0133378 A1 * 5/2015 Murphy ............. G01N 33/6893 514/7.7
2016/0024581 A1 * 1/2016 Sarwal ................. C12Q 1/6883 435/6.12
2016/0283679 A1 * 9/2016 Hu ........................... G06N 7/01
2016/0283686 A1 * 9/2016 Hu ......................... G16H 50/30
2016/0358290 A1 * 12/2016 Chiu ...................... G16H 50/30
2017/0022280 A1 * 1/2017 Jordan ............... C07K 16/2866
2017/0030928 A1 * 2/2017 Reed .................. C07K 14/8121
2017/0032090 A1 * 2/2017 Kamen ...................... G06N 20/00
2017/0089919 A1 * 3/2017 Bestard Matamoros .................... G01N 33/56977
2017/0114407 A1 * 4/2017 Murphy ............... C12Q 1/6883
2017/0342494 A1 * 11/2017 Brouard ............... G01N 33/502
2018/0143206 A1 * 5/2018 Anglicheau ........ A61K 39/3955
2018/0193437 A1 * 7/2018 Lucas .................. A61K 39/275
2018/0292395 A1 * 10/2018 Murphy .................. A61P 13/12
2019/0032135 A1 * 1/2019 Salomon .............. C12Q 1/6883
2019/0295252 A1 * 9/2019 Fuchs ................ G06V 10/7635
2020/0152334 A1 * 5/2020 Singh ..................... G16H 50/70
2020/0219249 A1 * 7/2020 Labiche ................ G06T 7/0012
2020/0399700 A1 * 12/2020 Salomon .............. C12Q 1/6883
2021/0070853 A1 * 3/2021 Chow ..................... A61P 37/06
2021/0158524 A1 * 5/2021 Madabhushi ......... G06T 7/0014
2021/0198733 A1 * 7/2021 Moshkevich ........ C12Q 1/6869
2021/0222240 A1 * 7/2021 Moshkevich ........ C12Q 1/6869
2021/0230700 A1 * 7/2021 Murphy ............... C12Q 1/6883
2022/0068480 A1 * 3/2022 Manzi .................. G06T 7/0012
2022/0073605 A1 * 3/2022 Jordan ............... A61K 39/3955
2022/0120761 A1 * 4/2022 Sarwal ................... G16B 40/20
2022/0135695 A1 * 5/2022 Jordan .................... A61P 37/06 424/142.1
2022/0293274 A1 * 9/2022 Loupy .................... G16H 20/40
2022/0333198 A1 * 10/2022 Lambrechts ......... C12Q 1/6883
2022/0405917 A1 * 12/2022 Madabhushi .......... G16H 10/40
2023/0029915 A1 * 2/2023 Vladimirova .......... G16H 50/20
2023/0059874 A1 * 2/2023 Borràs Serres .... G01N 33/6893
2023/0162860 A1 * 5/2023 Anglicheau ........ G01N 33/6863 705/2
2023/0169652 A1 * 6/2023 Kazemzadeh ......... G16H 50/20 382/128
2023/0215576 A1 * 7/2023 Loupy .................... G16H 50/30 702/19
2023/0245782 A1 * 8/2023 Zimmerman ......... G06F 18/214 600/301
2023/0287497 A1 * 9/2023 Moshkevich .......... C12Q 1/686
2023/0374595 A1 * 11/2023 Salomon .............. C12Q 1/6883
2023/0381271 A1 * 11/2023 Martin .................. G01N 33/62
2024/0038335 A1 * 2/2024 Nance .................... G16H 50/20
2024/0071621 A1 * 2/2024 Kim ....................... G16H 50/30
2024/0077469 A1 * 3/2024 Martin ............... A61K 31/5377
2024/0104894 A1 * 3/2024 Bai ...................... G06V 10/764
2024/0124573 A1 * 4/2024 Chow .................. C07K 16/248
2024/0132618 A1 * 4/2024 Steidl ................ C07K 16/2896
2024/0191301 A1 * 6/2024 Friedewald .......... C12Q 1/6883
2024/0212850 A1 * 6/2024 Marquet ................ G16H 50/20
2024/0228654 A9 * 7/2024 Steidl ................ C07K 16/2896
2024/0255520 A1 * 8/2024 Anglicheau ........ G01N 33/5005
2024/0285756 A1 * 8/2024 Berglund ........... C07K 16/2887
2024/0302385 A1 * 9/2024 Tanaka ................... G01N 33/68
2024/0331874 A1 * 10/2024 Rantalainen ........... G16H 50/20
2024/0387050 A1 * 11/2024 Zhang .................... G16H 15/00
2025/0003000 A1 * 1/2025 Moshkevich ........ C12Q 1/6869
2025/0006329 A1 * 1/2025 Burnett .................. G16H 70/60
2025/0014719 A1 * 1/2025 Su ......................... G16H 50/70
2025/0062032 A1 * 2/2025 Jain ........................ G16H 50/20
2025/0122576 A1 * 4/2025 Salomon .............. C12Q 1/6883
2025/0125054 A1 * 4/2025 Muhammad ........... G16B 20/00
2025/0166836 A1 * 5/2025 Foran ..................... G16H 10/20
2025/0197074 A1 * 6/2025 Loupy ................ B65D 17/4012
2025/0218591 A1 * 7/2025 Noth ...................... G16H 20/10
2025/0263480 A1 * 8/2025 Jordan ............. A61K 39/39516
2025/0276061 A1 * 9/2025 Berglund ............. A61K 31/436
2025/0285412 A1 * 9/2025 Bai ........................ G06V 10/72

OTHER PUBLICATIONS

Jeong, Kidney Res Clin Pract, 2020, pp. 17-31.*
Roufosse, 2018, Transplantation, pp. 1795-1814.*
Loupy et al: "The Banff 2019 Kidney Meeting Report (I): Updates on and clarification of criteria for T cell- and antibody-mediated rejection", American Journal of Transplantation, vol. 20, No. 9, p. 2318-2331, May 28, 2020.
Roufosse et al: "A 2018 Reference Guide to the Banff Classification of Renal Allograft Pathology", Transplantation, vol. 102, No. 11, p. 1795-1814, Nov. 30, 2018.
Anonymous: "Banff Classification—Wikipedia", https://en.wikipedia.org/w/index.php?title=Banff_Classification&oldid=951471191, Oct. 1, 2021.
Anonymous: "Gradient boosting—Wikipedia", https://en.wikipedia.org/w/index.php?title=Gradient_boosting&oldid=1016946224, Oct. 5, 2021.
Anonymous: "Machine learning—Wikipedia", https://en.wikipedia.org/w/index.php?title=Machine_learning&oldid=1020299340, Oct. 13, 2021.

* cited by examiner

COMPUTER-IMPLEMENTED DIAGNOSTIC METHOD FOR DETERMINING THE CLINICAL INTERPRETATION OF RENAL GRAFT ALTERATIONS

TECHNICAL FIELD

The invention relates to a computer-implemented diagnostic method for determining the clinical interpretation of renal graft alterations by applying a trained machine-learning model and a method for training a model for determining clinical categories based on renal transplant lesions, clinical signs and routine laboratory test results.

BACKGROUND OF THE INVENTION

The international Banff classification helps to standardize the diagnosis of different forms of renal allograft alteration. It is based on a grid of histological criteria ranking the extent of elementary lesions, with predefined thresholds. Subsequently, numerous rules must be applied to deduce, based on combinations of histological criteria, the following histological diagnoses: antibody-mediated rejection (ABMR); T cell-mediated rejection (TCMR); and interstitial fibrosis and tubular atrophy (IFTA). However, this gold-standard strategy is not perfect, and it is difficult to apply everywhere and at all times for several reasons. First, the interobserver reproducibility of reporting and ranking histological lesions is poor (Marcussen N. et al. Transplantation. 1995; 60(10): 1083-9; Furness P N, et al. Kidney Int. 2001; 60(5): 1998-2012; Furness P N, et al. Am J Surg Pathol. 2003; 27(6): 805-10). Secondly, the definition of the phenotypes based on histological lesion grading has evolved every other year since 2005, with each revision of the Banff classification. In small transplant centers where pathologists have a general practice, it is hard to integrate this flurry of information with the same level of expertise as pathologists specialized in analyzing kidney allograft biopsies. Third, centralized gold-standard graft biopsy reading is not always possible in academic-sponsored clinical studies in kidney transplantation (e.g., on biomarkers (Van Loon E et al. EBioMedicine. 2019 August; 46:463-72), treatment strategies, survival analyzes in prospective or retrospective cohorts) due to logistic and financial constraints.

Finally, the histological diagnosis is used by the transplant clinicians to pose their clinical diagnosis, also accounting for other laboratory test results (e.g., serum creatinine, proteinuria), the patient history and current clinical signs. The therapeutic actions are taken based on this final clinical diagnosis, the construction of which has never been codified.

SUMMARY OF THE INVENTION

In this context, artificial intelligence (AI) could help pathologists and clinicians in this part of their task, i.e. interpretation of the elementary histological lesions in the clinical context. Machine Learning (ML) is defined as a subset of the AI domain capable of automatically learning and continuously adapting the interpretation or prediction algorithms. Robust mathematical procedures are applied by computer systems to achieve these complex tasks. With sufficient data, it can handle noisy and correlated variables, sometimes without the need for parametric assumptions, contrary to most traditional statistics. As has been recognized at the last Banff Meeting (Loupy A, et al. Am J Transplant. 2020; 20(9):2318-31), the combination of quality and quantity about input data is key for achieving result quality using ML. Whatever the ML method used, it is therefore necessary to train the model on a large enough database of pathological cases, examined by a panel of experienced pathologists. The inventors built a robust and accurate ML model capable of automatic biopsy classification using variables selected among the Banff criteria and routine laboratory test results. The inventors by developing and using the present ML model surprisingly showed that the important criteria for determining each renal graft lesion did not overlap with those used in the Banff classification. This robust ML model allows to determine the different clinical diagnoses of renal graft lesions precisely in one time by taking into account both histopathological criteria, laboratory test results and the patient history. It offers a reproducible way to classify kidney graft biopsies in academic-sponsored clinical studies in kidney transplantation. Moreover, despite the fact that, as in usual practice, some scored biopsies had missing data, the performance of the present method was still very good when 2 data per biopsy were missing, and even sometimes 3 or 4.

The present invention relates to a computer-implemented diagnostic method for determining active antibody-mediated rejection (ABMR) in a post-renal transplanted subject comprising the steps of: a/ collecting a set of parameters including histopathologic Banff lesion scores from 0 to 3 in a renal graft biopsy of said subject wherein said Banff lesion scores are glomerulitis (g), peritubular capillaritis (ptc) and chronic transplant glomerulopathy (cg), and b/ determining by applying a trained machine-learning model on said set of parameters, whether a post-renal transplanted subject has active ABMR. In a preferred embodiment, said collected set of parameters on which the trained machine-learning model is applied comprises one or more set parameter(s) selected from the group consisting of: laboratory test result determining the presence of donor-specific antibodies (DSA), clinical data determining the time between transplantation and biopsy, histopathologic Banff lesion score from 0 to 3 of C4d staining in ptc or medullary vasa recta (C4d) in a renal graft biopsy, laboratory test result determining the concentration of serum creatine and laboratory test result determining the concentration of proteinuria. In a more preferred embodiment, said machine learning model has been trained by supervised learning on a training dataset comprising for each of a plurality of kidney biopsies, laboratory test results and clinical data of post-renal transplanted subjects, an assessment of each parameter of the set of parameters, and a clinical diagnosis of presence or absence of active ABMR provided by an expert.

The present disclosure also relates to a computer-implemented diagnostic method for determining chronic active antibody-mediated rejection (ABMR) in a post-renal transplanted subject comprising the steps of: a/ collecting a set of parameters including histopathologic Banff lesion score of chronic transplant glomerulopathy (cg) from 0 to 3 in a renal graft biopsy of said subject and clinical data determining the time between transplantation and said biopsy, and b/ determining by applying trained machine-learning model on said set of parameters whether a post-renal transplanted subject has chronic active ABMR, preferably said machine learning model has been trained by supervised learning on a training dataset comprising for each of a plurality of kidney biopsies and clinical data of post-renal transplanted subjects, an assessment of each parameter of the set of parameters and a clinical diagnosis of presence or absence of chronic active ABMR provided by an expert.

In another particular embodiment, the present invention relates to a computer-implemented diagnostic method for determining T-cell-mediated rejection (TCMR) in a post-renal transplanted subject comprising the steps of: a/ collecting a set of parameters including histopathologic Banff lesion scores from 0 to 3 of tubulitis in cortical tubules within non-scarred cortex (t) and inflammation in non-scarred cortex (i) in a renal graft biopsy of said subject, b/ determining by applying trained machine-learning model on said set of parameters, whether a post-renal transplanted subject has TCMR. Preferably said collected set of parameters on which the trained machine-learning model is applied further comprises histopathologic Banff lesion score from 0 to 3 of total cortical inflammation (ti) in a renal graft biopsy. In a preferred embodiment, said machine learning model has been trained by supervised learning on a training dataset comprising for each of a plurality of kidney biopsies of post-renal transplanted subjects, an assessment of each parameter of the set of parameters and a clinical diagnosis of presence or absence of TCMR provided by an expert.

The present invention also relates to a computer-implemented diagnostic method for determining interstitial fibrosis and tubular atrophy (IFTA) in a post-renal transplanted subject comprising the steps of: a/ collecting a set of parameters including histopathologic Banff lesion scores from 0 to 3 of tubular atrophy in cortex (ct) and preferably interstitial fibrosis in cortex (ci) in a renal graft biopsy of said subject, b/ determining by applying a trained machine-learning model on said set of parameters whether a post-renal transplanted subject has IFTA, preferably the machine learning model has been trained by supervised learning on a training dataset comprising for each of a plurality of kidney biopsies of post-renal transplanted subjects, an assessment of each parameter of the set of parameters and a clinical diagnosis of presence or absence of IFTA provided by an expert.

The present invention also relates to a computer-implemented diagnostic method for determining active antibody-mediated rejection (ABMR) in a post-renal transplanted subject as described above further comprising at least one computer-implemented diagnostic method selected from the group consisting of the method for determining chronic active ABMR, the method for determining TCMR according, and the method for determining IFTA as described above.

In another aspect, the present invention relates to a method for training a model for determining different clinical diagnoses for different combinations of transplant alterations, in particular selected from the group consisting of: antibody-mediated rejection (ABMR), T-cell-mediated rejection (TCMR), interstitial fibrosis and tubular atrophy (IFTA), chronic-active ABMR or active ABMR in a kidney transplant subject comprising the steps of: a. Collecting a training dataset comprising, for each of kidney transplant subjects: i. a set of histopathologic Banff lesion scores from 0 to 3 in a renal graft biopsy of said subject wherein the set of Banff lesion scores comprises: glomerulitis (g), peritubular capillaritis (ptc), linear C4d staining in ptc or medullary vasa recta (C4d), chronic transplant glomerulopathy (cg), inflammation in non-scarred cortex (i), tubulitis in cortical tubules within non-scarred cortex (t), total cortical inflammation (ti), tubular atrophy in cortex (ct) and interstitial fibrosis in cortex (ci), ii. a set of laboratory test results determining the presence of donor-specific antibodies (DSA), the concentration of serum creatinine or proteinuria in the subject at the time of the biopsy or the clinical data determining the time between transplantation and said biopsy, iii. an indication of the subject being subjected to at least one clinical diagnosis of renal transplant alteration among the renal transplant alteration diagnoses, b. for each clinical diagnosis of the above-mentioned group, training a machine learning model on the training dataset, wherein the machine learning model is configured to receive as input parameters a value of each histopathologic Banff lesion score of the set of histopathologic Banff lesion score and a value of each laboratory test result or clinical data of the set of routine laboratory test result, and to output an indication about the patient suffering or not from a renal transplant alteration of said clinical diagnosis. Preferably, according to the method, the machine learning model is a decision tree or a random forest and the training comprises performing Gradient Boosting. More preferably, the training dataset comprises for at least one subject, at most one or two missing values among the set of routine laboratory test result, clinical data and the set of Banff lesion scores.

In another aspect, the present invention relates to a computer program product comprising code instructions from implementing one of the methods cited above, when it is executed by a computer.

Finally, the present invention relates to a computer-implemented machine learning model trained according to the method as described above.

FIGURE LEGENDS

FIG. 1: ROC curve analysis in the training dataset. The accuracy was 0.97, 0.95, 0.99 and 0.94 for the clinical ABMR model, the clinical TCMR model, the clinical IFTA model and the clinical ABMR active/chronic model, respectively (arbitrary threshold set at 0.50).

Figure 2:
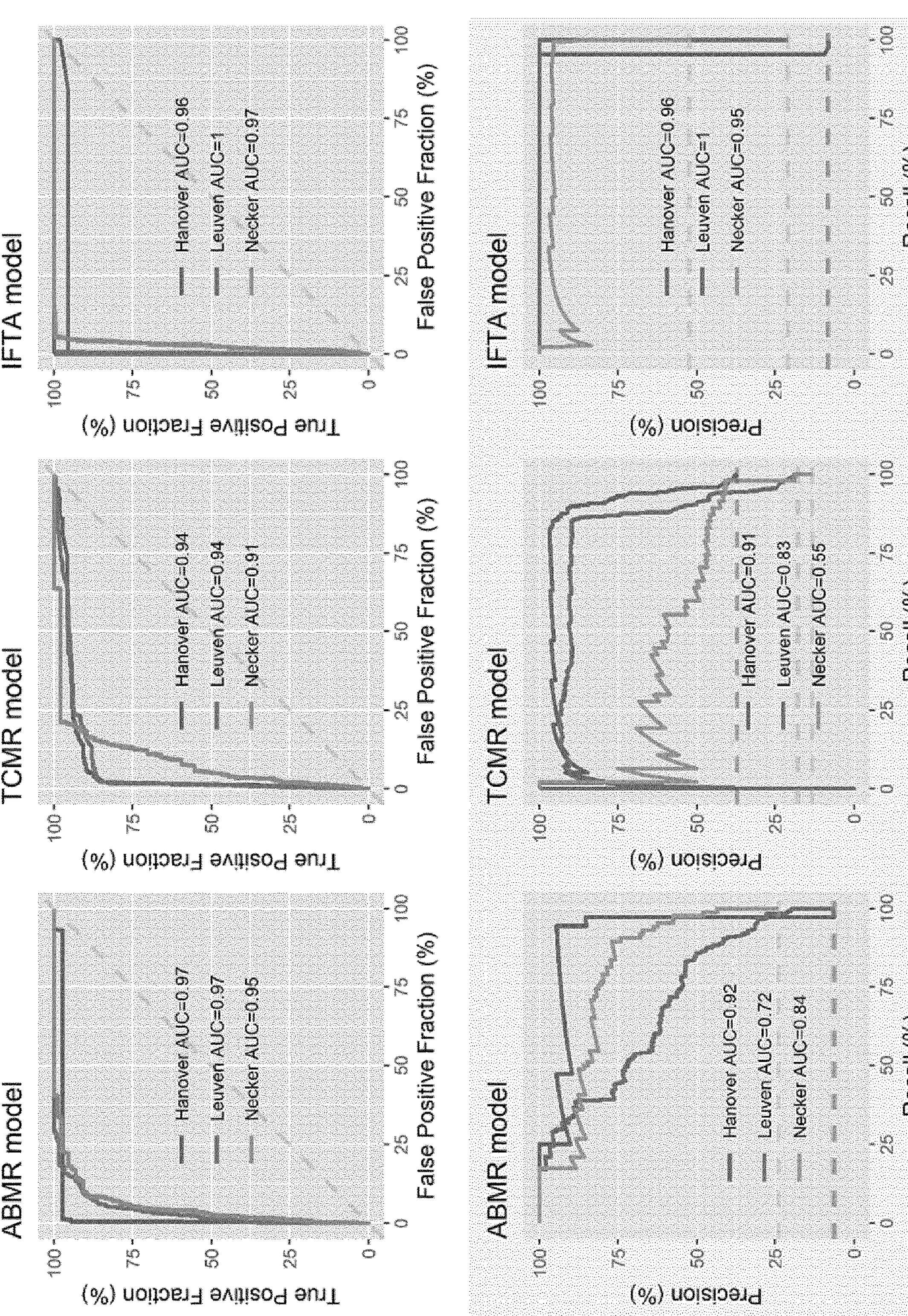

FIG. 2: External validation of the Machine Learning estimators in three independent cohorts. Abbreviations: ABMR, active antibody-mediated rejection; IFTA, interstitial fibrosis tubular atrophy grade II or more; Precision, positive predictive value; Recall, sensitivity; TOMR, T cell-mediated rejection.

Figure 3:
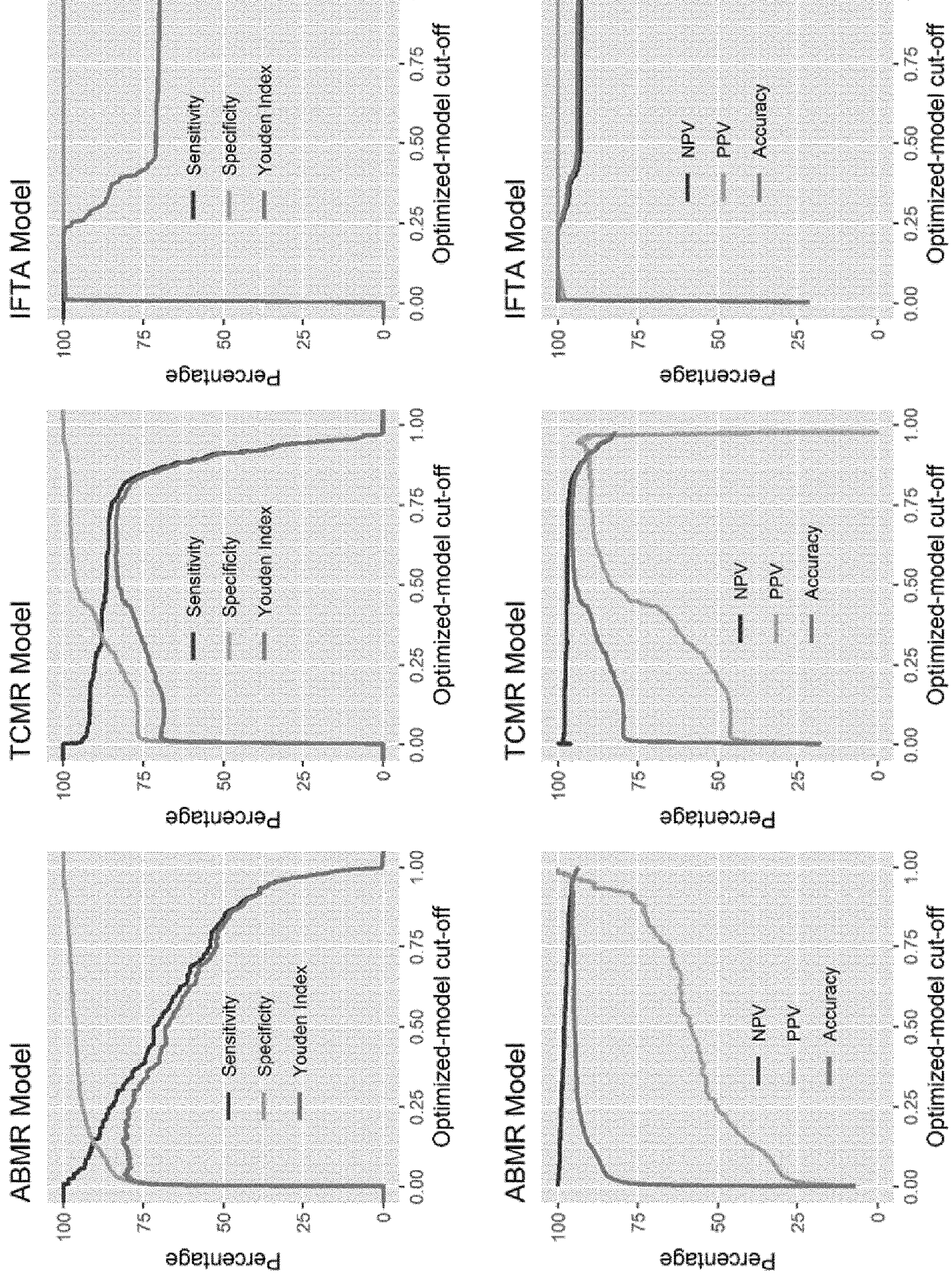
Figure 3:
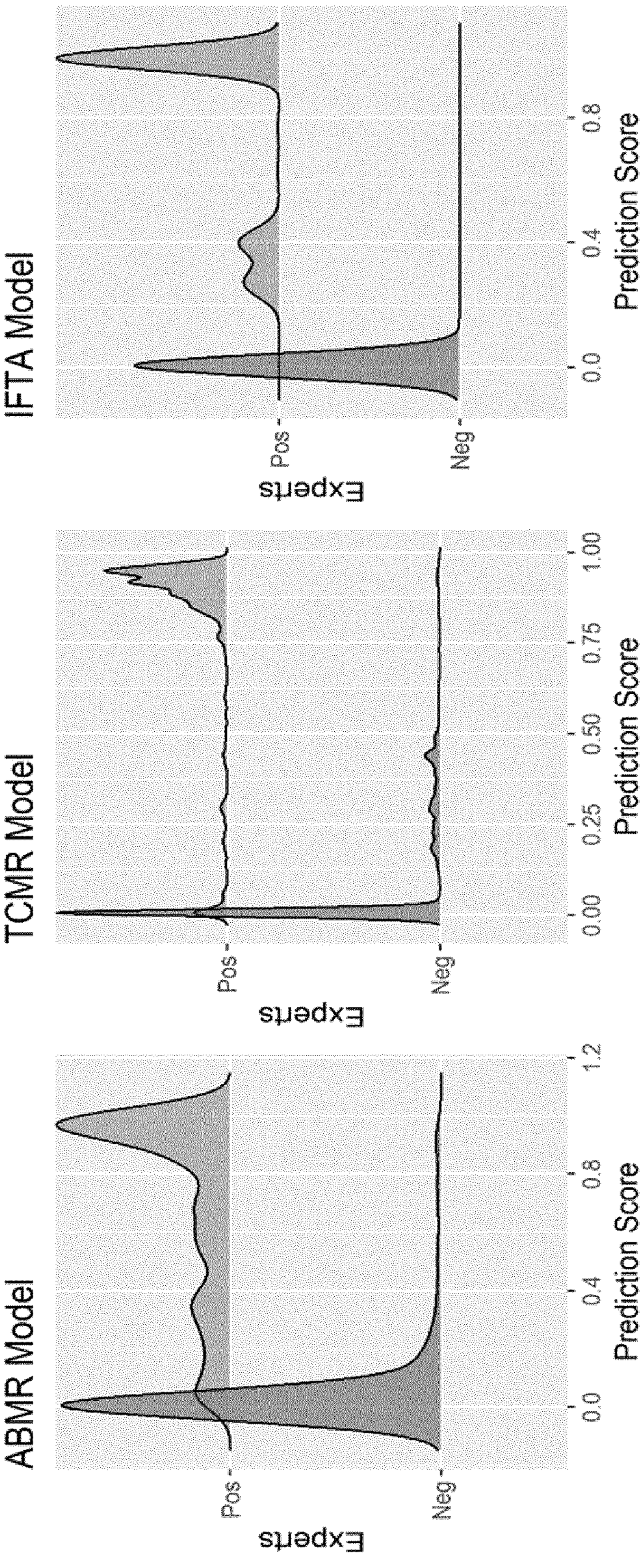

FIG. 3: Choice of the thresholds in the Leuven cohort. The plots at the bottom present the density of the scores. Abbreviations: ABMR, clinical active antibody-mediated rejection; IFTA, clinical interstitial fibrosis tubular atrophy grade II; NPV, negative predictive value; PPV, positive predictive value; TCMR, T cell-mediated rejection.

Figure 4:
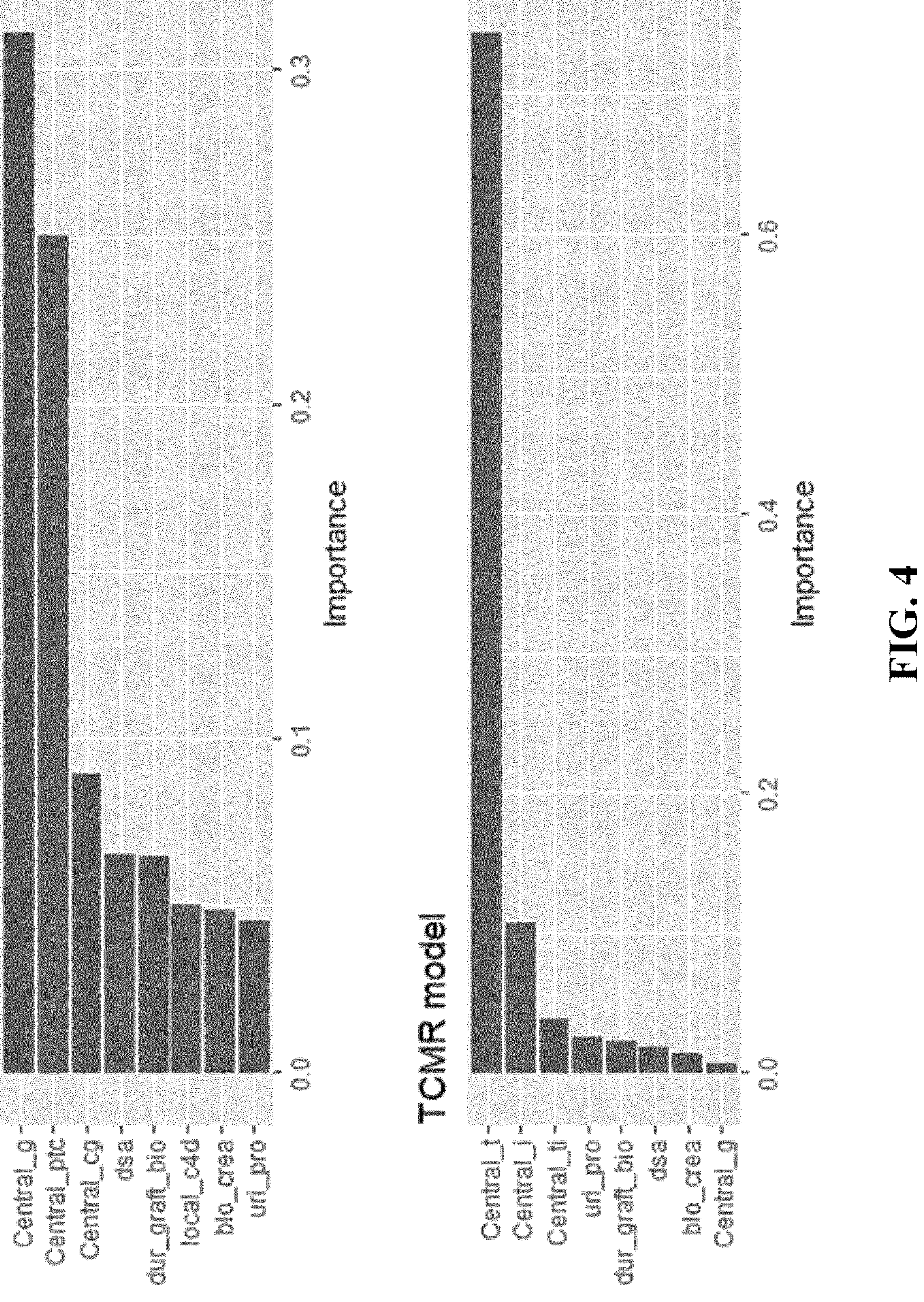
Figure 4:
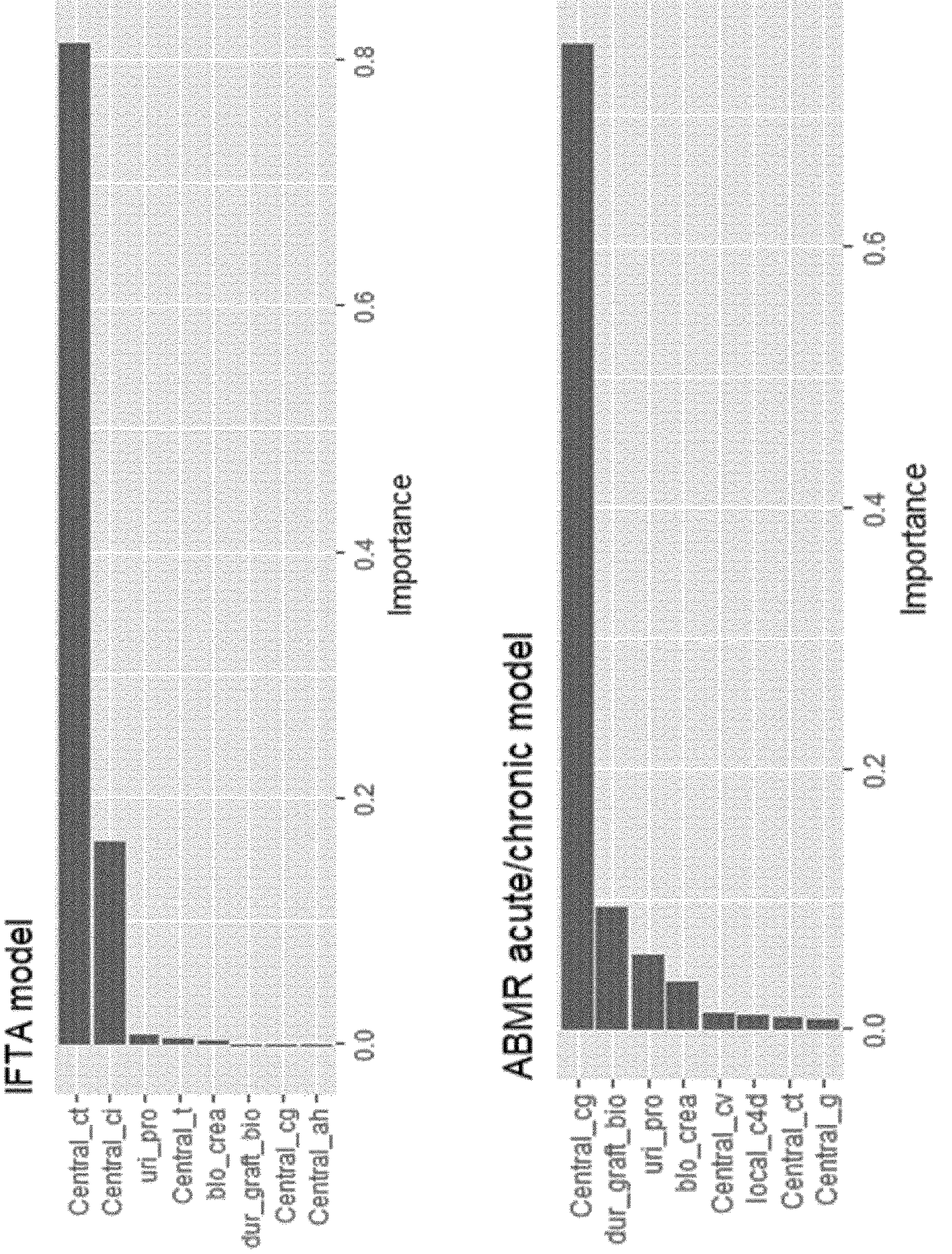

FIG. 4: Importance of the histological and clinical features for ML prediction. Importance provides a score that indicates how useful or valuable each feature was in the construction of the boosted decision trees within the model. The more an attribute is used to make key decisions with decision trees, the higher its relative importance.

DETAILED DESCRIPTION OF THE INVENTION

Renal transplantation is a treatment for patients with end-stage renal disease. However, a patient subjected to a renal graft can present graft alteration which is an immunologic reaction to donor antigens that are recognized by a recipient's immune system. Different pathologic changes associated with renal graft alteration can be observed and can be classified in the following diagnoses: acute and chronic active antibody-mediated rejection (ABMR), T-cell mediated rejection (TCMR) and interstitial fibrosis and tubular atrophy (IFTA).

The present disclosure relates to a computer-implemented diagnostic method for determining a renal transplant alteration clinical diagnosis such as active or chronic-active ABMR, TCMR or IFTA in a kidney transplant subject comprising the steps of collecting a set of parameters including histopathologic Banff lesion scores from 0 to 3 in a renal graft biopsy and, in some embodiments, routine laboratory test result and clinical data; and determining by applying a trained machine-learning model on said set of parameters the clinical diagnosis corresponding to the renal transplant alterations.

A biopsy of the grafted kidney is realized to analyze the presence or absence of several histological lesion types for evaluating graft alterations. The term "biopsy" refers to a specimen obtained by removing tissue from living patients for diagnostic examination. According to the present disclosure, the step of collecting a set of parameters does not comprise the step of biopsy and only refers to the in vitro or ex vivo evaluation of a set of parameters, such as the in vitro evaluation and score of histopathologic Banff lesion. According to the present disclosure, the step of collecting a set of parameters is not practiced on a human or animal body.

Biopsies histopathologic Banff lesions are evaluated and scored by renal pathologists between 0 to 3. The evaluation and score of the lesions are realized using international consensus Banff classification. Banff classification is well known from the skilled person in the art and presents a definition for each histologic injury, also named herein histopathological Banff lesion resulting from renal allograft rejections and provides a universal grading system for assessing theses injuries (see for example Roufosse C et al. 2018. Transplantation, 102(11):1795-1814; Jeong H J et al 2020, Kidney Res Clin. Pract. 39(1):17-31). In a particular embodiment, said Banff lesions are evaluated and scored by pathologists as recommended in the 2013 revised Banff classification (Haas M, et al. Am J Transplant Off J Am Soc Transplant Am Soc Transpl Surg. 2014; 14(2):272-83; Haas M. Am J Transplant Off J Am Soc Transplant Am Soc Transpl Surg. 2016 May; 16(5): 1352-7).

Histopathological Banff lesion score comprises: glomerulitis (g), peritubular capillaritis (ptc), linear C4d staining in ptc or medullary vasa recta (C4d), chronic transplant glomerulopathy (cg), inflammation in non-scarred cortex (i), tubulitis in cortical tubules within non-scarred cortex (t), total cortical inflammation (ti), tubular atrophy in cortex (ct) and interstitial fibrosis in cortex (ci). One way to evaluate and score criteria of each Banff lesions by experts such as pathologists in Haas M, et al. Am J Transplant Off J Am Soc Transplant Am Soc Transpl Surg. 2014; 14(2):272-83; Haas M. Am J Transplant Off J Am Soc Transplant Am Soc Transpl Surg. 2016 May; 16(5):1352-7, which are incorporated herein by reference and described briefly below.

Banff Lesion Score i (Interstitial Inflammation) evaluates the degree of inflammation in non-scarred areas of cortex. Score i0 corresponds to no inflammation or in less than 10% of unscarred cortical parenchyma, score i1 corresponds to inflammation in 10 to 25% of unscarred cortical parenchyma, score i2 corresponds to inflammation in 26 to 50% of unscarred cortical parenchyma and score i3 corresponds to inflammation in more than 50% of unscarred cortical parenchyma.

Banff Lesion Score t (Tubulitis) evaluates the degree of inflammation within the epithelium of the cortical tubules. Score to corresponds to no mononuclear cells in tubules or single focus of tubulitis only, score t1 corresponds to foci with 1 to 4 mononuclear cells/tubular cross section (or 10 tubular cells), score t2 corresponds to foci with 5 to 10 mononuclear cells/tubular cross section (or 10 tubular cells) and score t3 corresponds to foci with >10 mononuclear cells/tubular cross section or the presence of ≥2 areas of tubular basement membrane destruction accompanied by i2/13 inflammation and t2 elsewhere.

Banff lesion score g (glomerulitis) evaluates the degree of inflammation within glomeruli, in particular characterized by endothelial enlargement and inflammatory cell infiltration often resulting in capillary luminal narrowing and destruction. Score g0 corresponds to no glomerultis, score g1 to segmental or global glomerulitis in less than 25% of glomeruli, score g2 to segmental or global glomerulitis in 25 to 75% of glomeruli and score g3 to segmental or global glomerulitis in more than 75% of glomeruli.

Banff lesion score ptc (peritubular capillaritis) evaluates the degree of inflammation within peritubular capillaries (ptc), in particular characterized by endothelial enlargement and inflammatory cell infiltration. Score ptc0 corresponds to a maximum number of leukocytes <3, score ptc 1 corresponds to at least one leukocyte cell in ≥10% of cortical PTCs within 3-4 leukocytes in most severely involved PTC, score ptc2 corresponds to at least one leukocyte cell in ≥10% of cortical PTCs within 5-10 leukocytes in most severely involved PTC, score ptc3 corresponds to at least one leukocyte cell in ≥10% of cortical PTCs with >10 leukocytes in most severely involved PTC.

Banff lesion score ti (total inflammation) evaluates the extent of total cortical inflammation wherein all of the cortical parenchyma, including areas of interstitial fibrosis and tubular atrophy (IFTA), subcapsular cortex and perivascular cortex including nodular infiltrates are considered. Score ti1 corresponds to no or trivial interstitial inflammation (<10% of total cortical parenchyma), score ti1 corresponds to 10-25% of total cortical parenchyma inflamed, score ti2 corresponds to 26-50% of total cortical parenchyma inflamed and score ti3 corresponds to >50% of total cortical parenchyma inflamed.

Banff lesion score C4d evaluates the extent of staining for C4d on endothelial cells of PTCs and medullary vasa recta by immunostaining, for example immunohistochemistry or indirect immunofluorescence on sections of biopsies. C4d immunostaining is well known in the art and can be realized for example on snap frozen section of fresh biopsies or on formalin-fixated and paraffin-embedded tissue. Monoclonal or polyclonal C4d antibodies well known in the art can be used for immunostaining. Score C4d0 corresponds to no staining of PTC and medullary vasa recta, score C4d1 corresponds to minimal C4d staining (>0 but <10% of PTC and medullary vasa recta), score C4d2 corresponds to focal C4d staining (10-50% of PTC and medullary vasa recta), score C4d3 corresponds to diffuse C4d staining (>50% of PTC and medullary vasa recta).

Banff lesion score ci (interstitial fibrosis) evaluated the extent of cortical fibrosis. Score ci0 corresponds to interstitial fibrosis in up to 5% of cortical area, score ci1 corresponds to interstitial fibrosis in 6 to 25% of cortical area (mild interstitial fibrosis), score ci2 corresponds to interstitial fibrosis in 26 to 50% of cortical area (moderate interstitial fibrosis) and score ci3 corresponds to interstitial fibrosis in >50% of cortical area (severe interstitial fibrosis).

Banff lesion score ct (tubular atrophy) evaluates the extent of cortical tubular atrophy which is usually tightly associated with the areas affected with interstitial fibrosis. Score ct0 corresponds to no tubular atrophy, score ct1 corresponds to tubular atrophy involving up to 25% of the area of cortical tubules, score ct2 corresponds to tubular atrophy involving 26 to 50% of the area of cortical tubules, score ct3 corresponds to tubular atrophy involving in >50% of the area of cortical tubules.

Banff lesion cg (Glomerular basement membrane double contours) is based on the presence and extent of glomerular basement membrane (GBM) double contours or multi-lamination in the most severely affected glomerulus. Scoring can be carried out on periodic acid-Schiff (PAS) or silver stain. Score cg0 corresponds to no GBM double contours by light microscopy (LM) or electronic microscopy (EM), score cg1a corresponds to no GBM double contours by LM but GBM double contours (incomplete or circumferential) in at least 3 glomerular capillaries by EM, with associated endothelial swelling and/or subendothelial electron-lucent widening, score cg1b corresponds to double contours of the GBM in 1-25% of capillary loops in the most affected nonsclerotic glomerulus by LM; EM confirmation is recommended if EM is available, score cg2 corresponds to double contours affecting 26 to 50% of peripheral capillary loops in the most affected glomerulus, score cg3 corresponds to double contours affecting more than 50% of peripheral capillary loops in the most affected-glomerulus.

The set of collected parameters can comprise at least one or more, or all the above-recited Banff lesions scores.

The set of parameters collected can further comprise in vitro routine laboratory test result such as detection of donor-specific antibodies (DSA), quantification of serum creatinine or proteinuria of the patient at the time of the biopsy, and clinical data such as the time between transplantation and the biopsy. The detection of DSA can be realized as non-limiting examples by the complement-dependent lymphocytotoxicity (CDC) cross matching (XM) test, flow cytometry XM test, ELISA assay or multiplexed particle-based flow cytometry (e. g. Luminex test). The quantification of serum creatinine or proteinuria can be realized by any method well known in the art such as colorimetric, enzymatic or chromatographic assay.

In normal subject, the concentration of serum creatine is comprised between 45 and 84 μmol/L for women, and between 59 and 104 μmol/L for men, and proteinuria <0.10 g/L.

Once the set of parameters as described above is collected, the clinical diagnosis corresponding to the renal transplant alterations is determined by applying a trained machine-learning model on said set of parameters.

The machine-learning model is a binary classification model configured for determining, for one type of renal transplant alteration among active ABMR, chronic active ABMR, TCMR and IFTA, presence or absence of said renal transplant diagnosis. In embodiments, one machine learning model is trained for each of said renal transplant alteration diagnoses.

In embodiments, each machine learning model is a decision tree or a random forest.

As disclosed in more details below, each machine learning model is trained on a training dataset for which each parameter of the set of parameters recited above has been evaluated.

In particular, the training dataset comprises, for a plurality of patients:

- a score from 0 to 3 of each histopathologic Banff lesion score of the set of parameters, said score being provided by a group of experts and consensually interpreted, and
- a value of the routine laboratory test result of the set of parameters, which can include donor-specific antibodies detection, serum creatinine quantification, and proteinuria quantification and a value of clinical data determining the time between transplantation and biopsy.

In embodiments, for each machine learning model corresponding to each clinical diagnosis of renal transplant alteration, the training dataset may comprise the score from 0 to 3 of each histopathological Banff lesion score of the Banff classification, and the value of all the routine laboratory test result and clinical data parameters recited above. However, as described in more details below, it appears that, for each diagnosis of renal transplant alteration, some parameters are less relevant and hence the corresponding model may be trained on a reduced set of parameters comprising only a subset of those Banff classification, routine laboratory test results and clinical data which are the most relevant for the corresponding alteration category.

For each patient, the training dataset also comprises a category of renal transplant alteration provided by a pathologist, i.e., for each type of renal transplant alteration, an indication of the subject being subjected or not to said renal transplant alteration.

The machine learning model for each clinical diagnosis of renal transplant alteration is trained by supervised training on the training dataset. To this end, the training dataset is divided as known in the art into a learning subset and a validation subset. As the training dataset may not include the value of each parameter of the set for all the patients, the training of each model may preferably be performed by Gradient Boosting or Extreme Gradient Boosting (XGBoost), which enables training the model even on data for which one or two parameter values are missing.

In a particular embodiment, the present disclosure relates to a computer-implemented diagnostic method for determining active antibody-mediated rejection (ABMR) in a post-renal transplanted subject comprising the steps of:

a. collecting a set of parameters including histopathologic Banff lesion scores from 0 to 3 in a renal graft biopsy of said subject wherein said Banff lesion scores are glomerulitis (g), peritubular capillaritis (ptc) and chronic transplant glomerulopathy (cg), and
b. determining by applying a trained machine-learning model on said set of parameters, whether a post-renal transplanted subject has active ABMR.

The machine learning model used in this method has been trained by supervised learning on a training dataset comprising for each of a plurality of kidney biopsies, laboratory test results and clinical data of post-renal transplanted subjects, an assessment of each parameter of the set of parameters, and a clinical diagnosis of presence or absence of active ABMR provided by an expert, such as a pathologist.

In embodiments, the collected set of parameters comprises all the histopathological Banff lesion scores, as well as all the laboratory test results and clinical data parameters recited above. In this case, the machine-learning model is trained on a training dataset comprising, for a plurality of patients, the same set of parameters.

The first chart of FIG. 4 shows the relative importance of parameters used by the machine learning model for determining active ABMR, when said model is trained on a set of parameters including all the parameters of the Banff classification (g, ptc, C4d, cg, v, I, t, ti, ct, ci, ah, cv) as well as all the laboratory test result and clinical data parameters recited above. Surprisingly enough, one can notice this chart shows that the most relevant parameters for determining active ABMR are glomerulitis g, peritubular capillaritis ptc and chronic transplant glomerulopathy cg. However, chronic transplant glomerulopathy ptc is not used, according to the Banff classification, for establishing active ABMR, it is only used for differentiating between chronic and non-chronic ABMR. It can also be noted that the Banff lesion score of endarteritis (v) does not appear as an important parameter for determining ABMR, whereas it is of equivalent importance than the parameters g and ptc according to the Banff classification. Therefore, this parameter may, according to the disclosed method, be ignored for both training and inference of the model.

In embodiments, the collected set of parameters may only comprise the three parameters cited above, as they are the most important (as shown in FIG. 4) for determining active ABMR. However, for enhanced performance, the collected set of parameters and on which the trained machine-learning model is applied may further comprise one or more of the parameter(s) selected from the group consisting of: laboratory test result determining the presence of donor-specific antibodies (DSA), clinical data determining the time between transplantation and biopsy, histopathologic Banff lesion score from 0 to 3 of C4d staining in ptc or medullary vasa recta (C4d) in a renal graft biopsy, laboratory test result determining the concentration of serum creatinine and laboratory test result determining the concentration of proteinuria.

In a preferred embodiment, the collected set of parameters and on which the trained machine-learning model is applied further comprises laboratory test result determining the presence of donor-specific antibodies (DSA) and clinical data determining the time between transplantation and biopsy, more preferably laboratory test result determining the presence of donor-specific antibodies (DSA), clinical data determining the time between transplantation and biopsy and histopathologic Banff lesion score from 0 to 3 of C4d staining in ptc or medullary vasa recta (C4d) in a renal graft biopsy, again more preferably laboratory test result determining the presence of donor-specific antibodies (DSA), clinical data determining the time between transplantation, biopsy and histopathologic Banff lesion score from 0 to 3 of C4d staining in ptc or medullary vasa recta (C4d) in a renal graft biopsy and laboratory test result determining the concentration of serum creatinine.

In a more preferred embodiment, the collected set of parameters and on which the trained machine-learning model is applied further comprise laboratory test result determining the presence of donor-specific antibodies (DSA), clinical data determining the time between transplantation, biopsy and histopathologic Banff lesion score from 0 to 3 of C4d staining in ptc or medullary vasa recta (C4d) in a renal graft biopsy, laboratory test result determining the concentration of serum creatinine and laboratory test result determining the concentration of proteinuria.

In order to characterize in one time the different graft alterations in the post-transplanted subject, said computer-implemented diagnostic method for determining ABMR as above further comprises a computer-implemented diagnostic method for determining chronic active ABMR, TCMR and/or IFTA as described below. The method is thus particularly advantageous to determine at the same time different clinical diagnoses of renal allograft alteration in a post-renal transplanted subject.

The present disclosure relates to a computer-implemented diagnostic method for determining chronic active antibody-mediated rejection (ABMR) in a post-renal transplanted subject comprising the steps of:

a. collecting a set of parameters including histopathologic Banff lesion score of chronic transplant glomerulopathy (cg) from 0 to 3 in a renal graft biopsy of said subject and clinical data determining the time between transplantation and said biopsy, and
b. determining by applying trained machine-learning model on said set of parameters whether a post-renal transplanted subject has chronic active ABMR.

In a particular embodiment, the machine learning model used in the method for determining chronic ABMR as described above has been trained by supervised learning on a training dataset comprising for each of a plurality of kidney biopsies and clinical data of post-renal transplanted subjects, an assessment of each parameter of the set of parameters, and a clinical diagnosis of presence or absence of chronic ABMR provided by an expert. In other embodiments, the machine learning model may be trained on a set of parameters including additional parameters, and, for instance, including the score ranging from 0 to 3 all the parameters of the Banff classification and all the laboratory test result and clinical data parameters recited above.

The fourth chart of FIG. 4 represents the relative importance of parameters used by the machine learning model for determining chronic ABMR, when said model has been trained on a set of parameters including all the parameters of the Banff classification, as well as all the laboratory test result and clinical data parameters recited above. One can notice that the parameters used by the model do not have the same importance as according to the Banff classification rules. In particular, the clinical data parameters of time elapsed between the transplant and the biopsy, laboratory results determining concentration of proteins in urine (proteinuria) and creatinine in plasma are parameters which are not used according to the Banff classification rules for determining chronic ABMR, but which for the model, have more importance than the criterion v of endarteritis, which is also used for determining chronic ABMR according to Banff classification rules. This chart of relative importance of parameters shows that cg and time between the transplant and the biopsy are the most important for determining chronic ABMR and, in some embodiments, may be sufficient for such determination.

In embodiments, the collected set of parameters, used for the training of the model and for inference, may also comprise proteinuria and creatinine, for increased performance. In embodiments, the collected set of parameters may consist in cg, time between the transplant and the biopsy, concentration of proteins in urine and creatinine in plasma.

In another embodiment, the present disclosure relates to a computer-implemented diagnostic method for determining T-cell-mediated rejection (TCMR) in a post-renal transplanted subject comprising the steps of:

a. collecting a set of parameters including histopathologic Banff lesion scores from 0 to 3 of tubulitis in cortical tubules within non-scarred cortex (t) and inflammation in non-scarred cortex (i) in a renal graft biopsy of said subject,
b. determining by applying trained machine-learning model on said set of parameters, whether a post-renal transplanted subject has TCMR.

In a particular embodiment, the machine learning model used in this method for determining TCMR has been trained by supervised learning on a training dataset comprising for each of a plurality of kidney biopsies, laboratory test results and clinical data of post-renal transplanted subjects, an assessment of each parameter of the set of parameters, and a clinical diagnosis of presence or absence of TCMR provided by an expert.

In a preferred embodiment, the collected set of parameters and on which the trained machine-learning model is applied further comprises histopathologic Banff lesion score from 0 to 3 of total cortical inflammation (ti) in a renal graft biopsy.

In embodiments, the collected set of parameters, on which the model is applied, and on which the model has been trained, comprises the scores from 0 to 3 of all the histopathological Banff lesion score of the Banff classification, and all the laboratory test results and clinical data parameters recited above.

The second chart of FIG. 4 represents the relative importance of parameters used by the machine learning model for determining TCMR, when said model has been trained on a set of parameters including all parameters of the Banff classification, as well as the laboratory test results and clinical data parameters recited above. One can notice that the parameters used by the model do not have the same importance as according to the Banff classification rules. In particular, parameter t has a lot more importance than parameter i, whereas according to the Banff classification rules these two parameters have equal importance. The model may even be trained and used only on those two most important parameters, as noted above. It should also be noted that, whereas according to the Banff classification rules, an augmentation of the parameter v can itself determine TCMR, this parameter v does not appear among the most important parameters used by the machine learning model and can even be ignored.

The present disclosure also relates to a computer-implemented diagnostic method for determining interstitial fibrosis and tubular atrophy (IFTA) in a post-renal transplanted subject comprising the steps of:

a. collecting a set of parameters including histopathologic Banff lesion scores from 0 to 3 of tubular atrophy in cortex (ct) in a renal graft biopsy of said subject,
b. determining by applying a trained machine-learning model on said set of parameters whether a post-renal transplanted subject has IFTA.

In embodiments, the collected set of parameters may only comprise the parameter cited above, as it is the most important (as shown in FIG. 4) for determining IFTA. However, for enhanced performance, in a preferred embodiment, the collected set of parameters and on which the trained machine-learning model is applied may further comprises histopathologic Banff lesion scores from 0 to 3 of interstitial fibrosis in cortex (ci).

In a particular embodiment, the machine learning model used in the method for determining IFTA as described above has been trained by supervised learning on a training dataset comprising for each of a plurality of kidney biopsies, laboratory test results and clinical data of post-renal transplanted subjects, an assessment of each parameter of the set of parameters, and a clinical diagnosis of presence or absence of active IFTA provided by an expert.

In embodiments, the collected set of parameters, on which the model is applied, and on which the model has been trained, comprises the scores from 0 to 3 of all the histopathological Banff lesion score of the Banff classification, and all the laboratory test results and clinical data parameters recited above.

The third chart of FIG. 4 represents the relative importance of parameters used by the machine learning model for determining IFTA, when said model has been trained on a set of parameters including all parameters of the Banff classification, as well as the laboratory test results and clinical data parameters recited above. One can notice that the parameters used by the model do not have the same importance as according to the Banff classification rules. In particular, according to the Banff classification rules, tubular atrophy in cortex ct and interstitial fibrosis in cortex ci are equivalent in importance for determining IFTA, whereas the machine learning model relies much more predominantly in ct parameter than in ci parameter.

The determination of IFTA by using only ct parameter, is particularly advantageous as in usual practice, some scored biopsies had missing data. Thus, the determination of IFTA lesion using the machine learning model was still very good when ci parameter was missing.

In embodiments, the collected set of parameters for training and applying the machine learning model may consist in the score between 0 and 3 of ct alone. In embodiments and for improved precision, the collected set of parameters for training and applying the model may consist in the score between 0 and 3 of ct and ci only.

Method of Treatment

In connection with above methods for determining clinical diagnoses of renal transplant alteration, the present disclosure relates to the treatment of the renal graft alteration of a subject previously classified as having said specific renal graft alteration using the method for determining corresponding renal graft alteration as described above.

The present disclosure relates to a method of treating renal graft alteration in post-renal transplanted subject comprising determining said renal graft alteration diagnosis by the method as described above and administering to said subject a therapeutically effective amount of an immunosuppressive agent or submitting said subject to immunosuppressive treatment.

As used herein, a "therapeutically effective amount" or an "effective amount" means the amount of a composition that, when administered to a subject for treating a state, disorder or condition is sufficient to affect a treatment. The therapeutically effective amount will vary depending on the compound, formulation or composition, the disease and its severity and the age, weight, physical condition and responsiveness of the subject to be treated.

By "kidney transplant subject" or "post-renal transplanted subject", it is intended a subject, preferably a patient who has undergone a kidney transplant. Said patient is, in particular, patients with end-stage renal disease before transplantation.

As used herein, the term "treatment", "treat" or "treating" refers to any act intended to ameliorate the health status of patients such as therapy, prevention, prophylaxis and retardation of the disease. In certain embodiments, such term refers to the amelioration or eradication of a disease or symptoms associated with a disease. In other embodiments, this term refers to minimizing the spread or worsening of the disease resulting from the administration of one or more therapeutic agents to a subject with such a disease.

Immunosuppressive treatment is a treatment that lowers the activity of the subject's immune system. By immunosuppressive treatment, it is intended the administration of immunosuppressive agent but also extracorporeal treatment such as plasmapheresis or immunoadsorption.

Immunosuppressive agents are drugs that inhibit or prevent activity of the immune system. Said immunosuppressive agents can be as non-limiting examples glucocorticoid such as glucocorticoid which suppress the cell-mediated immunity by inhibiting genes coding for interleukins and TNF-alpha or suppress the humoral immunity, antibodies such as polyclonal antibodies which inhibit T lymphocytes and cause their lysis (e.g. antilymphocyte (ALG), antithymocyte antigens (ATG), monoclonal antibodies, preferably T-cell receptor directed antibodies, IL-2 receptor directed antibodies (anti-CD25 antibody), or B-cell directed antibodies and drugs that act on immunophilins such as calcineurin inhibitors (e.g. ciclosporin, tacrolimus).

Plasmapheresis refers to a process in which the liquid part of the blood or plasma is separated from the blood cells, and is replaced with another solution such as saline or albumin or the plasma is treated and then returned to the body of said patient. Immunoadsorption refers to a selective apheresis method for the removal of specific antibodies and immune complex, leaving other plasma components and obviating the need for plasma replacement.

In particular, the present disclosure relates to a method of treating ABMR, including chronic ABMR in a post-renal transplanted subject comprising determining ABMR or chronic ABMR in a post-renal transplanted subject by the method as described above and administering to said subject a therapeutically effective amount of immunosuppressive agent, preferably glucocorticoids, intravenous immunoglobulin, T cell- or B cell-depleting agent (i.e. rituximab) or by submitting said subject to plasmapheresis or immunoadsorption.

Glucocorticoids can be prednisone or prednisolone. B-cell depleting agent can be an antibody that binds B-cell surface molecules such as CD19, CD20 and CD22, in particular said B-cell depleting agent is a monoclonal anti-CD19 or anti-CD20 antibody such as rituximab or ocrelizumab and monoclonal anti-CD22 antibody such as epratuzumab, preferably monoclonal anti-CD20 antibody such as rituximab. T-cell depleting agent can be anti-thymocyte globulin (ATG) or an antibody that binds T-cell surface molecules such as CD3, CD4 or CD8, preferably anti-thymocyte globulin (ATG).

The present disclosure relates also to a method of treating TCMR in a kidney transplant subject comprising determining TCMR in a kidney transplant subject by the method as described above and administering in said subject a therapeutically effective amount of immunosuppressive agent, preferably glucocorticoids, T-cell depleting agent such as anti-thymocyte globulin and/or a calcineurin inhibitor. Said calcineurin inhibitor can be for example tacrolimus (FK-506) or cyclosporin.

The present disclosure also relates to a method of treating IFTA in a kidney transplant subject comprising determining IFTA in a kidney transplant subject by the method as described above and administering in said subject a therapeutically effective amount of immunosuppressive agent, preferably wherein said immunosuppressive agent is not a calcineurin inhibitor, or when said immunosuppressive agent is calcineurin inhibitor said calcineurin inhibitor is at low concentration, preferably between 3 to 7 ng/ml for tacrolimus or 50-70 ng/ml for cyclosporine.

The immunosuppressive agent described herein may be administered by any means known to those skilled in the art, including, without limitation, intravenously, orally, intratumoral, intra-lesional, intradermal, topical, intraperitoneal, intramuscular, parenteral, subcutaneous and topical administration. Thus, the compositions may be formulated as an injectable, topical, ingestible, or suppository formulation. Administration of the immunosuppressive agent to a subject in accordance with the present invention may exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage of immunosuppressive agent administered in any given case will be adjusted in accordance with the composition or compositions being administered, the volume of the composition that can be effectively delivered to the site of administration, the disease to be treated or inhibited, the condition of the subject, and other relevant medical factors that may modify the activity of the compositions or the response of the subject, as is well known by those skilled in the art.

For example, the specific dose of immunosuppressive agent for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological protocol. The compositions can be given in a single dose schedule, or in a multiple dose schedule.

Suitable dosage ranges for an immunosuppressive agent may be of the order of several hundred micrograms of the agent with a range from about 0.001 to 10 mg/kg/day, preferably in the range from about 0.01 to 1 mg/kg/day.

The invention will now be exemplified with the following examples, which are not limitative.

EXAMPLES

1. Methods 1.1 Patients and Biopsies

Histological data from kidney graft biopsies came from different independent datasets, in the form of the elementary Banff scores and diagnoses, as interpreted by pathologists. For the training set, the inventors used biopsy data from our BIOMArkers of Renal Graft INjuries (BIOMARGIN, www.biomargin.eu, ClinicalTrials.gov, number NCT02832661) European program aiming at discovering and validating robust non-invasive biomarkers (Marx D, et. Proteomics Clin Appl. 2019 March; 13(2): e1800091). The study was organized in several steps: the first two steps were case-control studies enabling the untargeted search and then the selection of a broad list of biomarkers. The third, cross-sectional step aimed to validate the diagnostic performance of the biomarker candidates on a representative sample of transplant patients in Europe. Between June 2011 and August 2016, more than 650 sample triplets (urine, blood and biopsy) were collected in highly standardized conditions and stored in the Biobanks of the four hospitals participating in the project (Hôpital Necker Paris, France; University Hospitals Leuven, Belgium; Medizinische Hochschule Hannover, Germany; and Centre Hospitalier Universitaire Limoges, France). All these biopsies were read and interpreted locally and then sent for central reading by an independent pathologist expert, with adjudication of discrepancies by consensus between three independent expert readers.

In the ROCKET project (Reclassification using OmiCs integration in KidnEy Transplantation, funded by ERACoSysMed 2018-2021), biopsy and omics data are being gathered to refine the definitions and discover accurate biomarkers of rarer phenotypes or graft lesions, including: active ABMR, active-chronic ABMR, acute TCMR, chronic TCMR, BK virus nephropathy and glomerulonephritis. Ambiguous cases or those with confounding conditions and lesions were excluded. This project provided us with a two-category ABMR definition (active/chronic active) used to train a more complex model.

For the external validation of the machine learning (ML) model and the choice of the thresholds, the inventors first used biopsy data from patients transplanted between 2004 and 2013 and followed-up until Sep. 1, 2019 at Katholieke Universiteit Leuven. The second validation dataset used was from patients followed-up from 2013 to 2019 at the Medizinische Hochschule Hannover. Finally, the third was from a single-center study at Hôpital Necker, Paris (7), approved by the ethics committee of Ile-de-France XI (13016), where clinically-indicated renal allograft biopsies were collected from February 2011 to February 2013.

For each biopsy, pathologist experts assessed the Banff criteria as recommended in the 2013 revised Banff Classification (8,9): glomerulitis (g), peritubular capillaritis (ptc), linear C4d staining in ptc or medullary vasa recta (C4d), chronic transplant glomerulopathy (cg), endarteritis (intimal arteritis, v), inflammation in non-scarred cortex (i), tubulitis in cortical tubules within non-scarred cortex (t), total cortical inflammation (ti), tubular atrophy in cortex (ct), interstitial fibrosis in cortex (ci), arteriolar hyalinosis (ah), arterial intimal fibrosis (fibrointimal thickening, cv). The diagnoses of interest were: active ABMR condition (yes/no), TCMR condition (yes/no, borderlines included as yes), IFTA condition (grade II was considered as positive). These diagnoses were considered as the reference (gold standard) for training the ML models in the BIOMARGIN datasets, and for validating them in the three independent datasets. The clinical databases included the laboratory test results about donor-specific antibodies (DSA), serum creatinine (umol/L) and proteinuria (g/L) at the time of the biopsy. All participating patients provided written informed consent.

1.2 Statistical Analyses

The predictors were the Banff criteria semi-quantitatively scored from 0 to 3 (g, ptc, C4d, cg, v, i, t, ti, ct, ci, ah, cv), DSA, serum creatinine, proteinuria, and time between transplantation and biopsy. From the training dataset, a ML algorithm was built for each different outcome: active ABMR (yes/no), TCMR (yes/no), IFTA (yes/no) and ABMR (active/chronic active). In the training dataset, biopsies with more than 3 missing data among the Banff criteria were removed. After analyzing the distribution of the Banff criteria, the inventors chose to impute the missing criteria (if no more than 2 per biopsy) by the respective median value. The ML technique of Gradient Boosting was chosen for its good performance and its ability to handle missing data for making predictions. Prior to training the algorithm, the inventors optimized the hyperparameters using ten-fold cross validation, for best accuracy. With this optimal set of hyperparameters, the inventors assessed the algorithm performance in the training phase using the same ten-fold cross validation. Receiver operating characteristic (ROC) curves were used to assess the classification performance of each model at various thresholds. True positive rate (sensitivity) and false positive rate (1-specificity) are represented in the y-axis and the x-axis, respectively. For imbalanced datasets, precision-recall (PR) curves are recommended too (10,11) as they do not require true negatives for their calculations. Precision (positive predictive value) and recall (sensitivity) are represented on the y-axis and the x-axis, respectively. Unlike ROC curve, the minimum PR area under the curve (AUC) is equal to the prevalence of the disease. In this study, the primary end points were the diagnostic accuracy and the ROC AUC of the different ML models.

The Leuven cohort was used to set thresholds based on the accuracy, predictive positive value, and predictive negative value in this cohort (12). These thresholds were then applied for external validation of the ML algorithm in the Hanover and Paris Necker cohorts.

For statistical computing and graphics, the inventors used the free software environment R (version 4.0.3) and especially the xgboost package for classification (version 1.2.0.1).

2. Results

In the BIOMARGIN training dataset (n=631), 73 biopsies missed one Banff criterion and 29 missed two. The patient clinical, histological, and biological characteristics at the time of allograft biopsy are presented in Table 1. Among the biopsies of the ROCKET dataset, 44 were chronic active ABMR.

TABLE 1

Patient characteristics, laboratory test results at the time of allograft biopsy and histological diagnoses.

| Variables | BIOMARGIN (training) (n = 631) | ROCKET (training) (n = 304) | KU Leuven (validation) (n = 3744) | MH Hanover (validation) (n = 589) | Necker Paris (validation) (n = 360) |
|---|---|---|---|---|---|
| Time after transplant (mo), median (IQR) | 12 (22) | 12 (40) | 12 (22) | 4 (10) | 12 (45) |
| Indicated biopsy, n (%) | 222 (35.2) | 134 (44.1) | 979 (26.1) | MD | MD |
| Pathologic primary diagnosis | | | | | |
| ABMR, n (%) | 104 (16.5) | 107 (35.2) | 242 (6.7) | 36 (6.1) | 86 (23.9) |
| TCMR, n (%) | 82 (13.0) | 84 (27.6) | 665 (17.8) | 193 (33.3) | 47 (13.1) |
| Mixed rejection, n (%) | 28 (4.4) | 19 (6.2) | 79 (2.1) | 15 (2.5) | 13 (3.6) |
| BKVN, n (%) | 0 (0.0) | 13 (4.3) | 124 (3.3) | 23 (4.1) | 11 (3.1) |
| IFTA, n (%) | 210 (33.3) | 98 (32.9) | 780 (20.8) | 44 (8.2) | 188 (52.2) |
| Normal, n (%) | 312 (49.4) | 93 (30.6) | 2420 (65.9) | 317 (57.3) | 133 (36.9) |
| Laboratory test results at the time of the biopsy | | | | | |
| Serum creatinine (μmol/L), median (IQR) | 150 (80) | 154 (89) | 141 (88) | 172 (103) | 176 (92) |
| DSA positivity, n (%) | 124 (19.7) | 87 (28.6) | 299 (8.3) | 11 (4.8) | 142 (41.0) |
| Proteinuria (g/L), median (IQR) | 0.10 (0.17) | 0.10 (0.27) | MD | 0.05 (0.06) | 0.20 (0.39) |

Abbreviations: ABMR, active antibody-mediated rejection; BKVN, BK virus nephropathy; DSAs, donor-specific antibodies; IFTA, interstitial fibrosis/tubular atrophy grade II; IQR, interquartile range; MD, missing data; TCMR, T cell-mediated rejection.

The detailed results of cross-validation in the training set are shown in FIG. 1. The ROC curves showed excellent performance with AUC of 0.99, 0.98 and 1.00 for the three binary models: ABMR, TCMR and IFTA, respectively. The calculated accuracy was 0.97, 0.95, 0.99 and 0.94 for ABMR, TCMR, IFTA and ABMR active/chronic active, respectively (arbitrary threshold set at 0.50).

Several analyses were performed to validate the ML algorithm, as shown in FIG. 2. For the ABMR model, the ROC curve AUC were 0.97, 0.97 and 0.95, the PR curve AUC were 0.92, 0.72 and 0.84 for the Hanover, Leuven, and Necker dataset, respectively, while the minimum AUC for a No-Skill Classifier were 0.06, 0.07 and 0.24, respectively. For the TCMR model, the ROC AUC were 0.94, 0.94 and 0.91, the PR AUC (minimum AUC for a No-Skill Classifier) were 0.91 (0.33), 0.83 (0.18) and 0.55 (0.13), respectively. For the IFTA model, the performance was even better with a minimum AUC of 0.95 between the ROC and PR curves, in all local datasets.

Thresholds were chosen so as to maximize accuracy in the Leuven cohort (FIG. 3). The inventors opted for a "grey zone" with two numerical cutoffs constituting its borders. The first cutoff was used to exclude the diagnosis with near certainty (to privilege sensitivity and negative predictive value), and the second to assert the diagnosis with similar near certainty (to privilege specificity and positive predictive value). The lower and upper thresholds were chosen at 0.10 and 0.75, respectively, for both binary models: ABMR and TCMR. Between these two thresholds, the ABMR grey zone includes 11.8, 0.6, and 2.1% of biopsies in the Leuven, Hanover, and Necker dataset, respectively; and the TCMR grey zone includes 18.5, 1.1, and 0.9% of biopsies, respectively. For IFTA the scores were already very well discriminated so the inventors choose a unique threshold of 0.10. The corresponding features of the models are presented in Table 2.

TABLE 2

Thresholds chosen for the different estimators

| | | ABMR model | | TCMR model | | IFTA model |
|---|---|---|---|---|---|---|
| | Threshold | Low = 0.10 | High = 0.75 | Low = 0.10 | High = 0.75 | Unique = 0.10 |
| Leuven | Sensitivity | 91.7 | 54.1 | 91.7 | 84.8 | 100.0 |
| | Specificity | 97.8 | 97.9 | 76.8 | 97.9 | 100.0 |
| | NPV | 99.3 | 96.8 | 97.7 | 96.8 | 100.0 |
| | PPV | 35.0 | 64.9 | 46.1 | 89.7 | 100.0 |
| | % cases between the two thresholds | 11.8 | | 18.5 | | NA |
| Hanover | Sensitivity | 97.2 | 91.7 | 90.2 | 82.3 | 95.5 |
| | Specificity | 95.7 | 99.6 | 92.0 | 98.4 | 100.0 |
| | NPV | 99.8 | 99.5 | 94.1 | 90.4 | 99.6 |
| | PPV | 59.3 | 94.3 | 87.0 | 96.7 | 100.0 |
| | % cases between the two thresholds | 0.6 | | 1.1 | | NA |
| Necker | Sensitivity | 98.8 | 89.5 | 91.5 | 42.6 | 99.5 |
| | Specificity | 65.0 | 90.9 | 80.5 | 91.8 | 94.8 |
| | NPV | 99.4 | 96.5 | 98.4 | 91.8 | 99.4 |
| | PPV | 47.0 | 75.5 | 41.3 | 62.5 | 95.4 |
| | % cases between the two thresholds | 2.1 | | 1.9 | | NA |

Abbreviations: NA, not applicable; NPV, negative predictive value; PPV, positive predictive value.

The Table 3 presents the performance of the ABMR active/chronic active estimator in the Leuven cohort. The accuracy was 0.98 for biopsies above the cutoff of 0.75, but also for biopsies above the lower cutoff of 0.10 (i.e., including the grey zone). The final accuracy of the two ABMR estimators (yes/no and active/chronic active) successively applied to the Leuven dataset was 0.95. In this case, the score thresholds were kept at 0.5 as these algorithms were already optimized to reach the best accuracy.

TABLE 3

Evaluation of the ML estimations of ABMR active/chronic active as compared with expert conclusions in the Leuven cohort (n = 232)

| | | | Experts conclusions | | |
|---|---|---|---|---|---|
| ABMR predicted in the "grey" zone (0.10 ≤ score < 0.75) | | | Active ABMR N = 79 | Chronic active ABMR N = 13 | Missing data N = 7 |
| Model predictions | Active ABMR | N = 88 | 79 | 2 | 7 |
| | Chronique active ABMR | N = 11 | 0 | 11 | 0 |
| ABMR predicted positive (scores ≥ 0.75) | | | Active ABMR N = 112 | Chronic active ABMR N = 19 | Missing data N = 2 |
| Model predictions | Active ABMR | N = 114 | 111 | 2 | 1 |
| | Chronique active ABMR | N = 19 | 1 | 17 | 1 |

Abbreviations: ABMR, antibody-mediated rejection.

DISCUSSION

Based on two large databases of kidney graft biopsy histological Banff scores obtained in state-of-the art conditions, the inventors have developed AI algorithm able to automatically derive the main alteration diagnoses from the histological Banff scores in standardized conditions. These algorithms showed excellent concordance with local biopsy reading by specialized pathologists in three large kidney transplant centers in Europe. Despite the fact that, as in usual practice, some scored biopsies had missing data in these different validation datasets, the performance of the estimators was still very good when no more than 2 data per biopsy were missing and even sometimes for 3 or 4 missing data.

Because the IFTA grade can be easily assessed using only two criteria of the Banff classification, it is not surprising that the present model almost never fails. At least, this study shows that no other criterion or laboratory test results influences the expert decision for this phenotype. It is also worth noting that this was the only perfectly reproducible phenotype across hospitals and pathologists in the present study. If the Banff classification were perfectly reproducible across pathologists in usual practice, the inventors could easily have been able to predict the different phenotypes with a ROC AUC of 1. Indeed, here the inventors used gradient boosting, an ensemble method literally based on decision trees.

Reproducibility has been assessed many times in the past, but only regarding the detection and grading of the elementary lesions. The diagnosis was not made by the pathologists themselves but calculated centrally using the Banff rules. For example, Marcussen et al. reported fair agreement for t, i and v, that were the only criteria used for grading the rejection at this period (Marcussen N, et al. Transplantation. 1995; 60(10):1083-9). The interobserver kappa score for grading the rejection severity was assigned centrally and was only 0.40 overall (fair agreement), it was 0.56 when only the presence or absence of acute rejection was considered (moderate agreement). Furthermore, agreement was poor for the ah and g criteria. The latter is essential for ABMR diagnosis. In the same way, the reproducibility of the criteria, with centralized final phenotypes, was studied by Smith et al too (Smith B, et al. Transpl Int Off J Eur Soc Organ Transplant. 2019 February; 32(2):173-83). In this study, a "majority rules" approach was successfully used to reduce variability, as it was here in the BIOMARGIN learning dataset. In the study of Furness et al (Furness P N, et al. Kidney Int. 2001; 60(5): 1998-2012), a reference diagnosis of acute rejection was set, based on the increase of serum creatinine in the week preceding the biopsy (or loss of the graft) with no other changes to explain the changes in creatinine. However, the criteria assessment was done blindly, meaning without considering any clinical features. Once again, the interpretation of the criteria was done automatically: only 74% and 47% of acute rejection episodes were detected, when the Banff "suspicious" grade was included or not, respectively. Gough (Gough J, et al. Nephrol Dial Transplant Off Publ Eur Dial Transpl Assoc—Eur Ren Assoc. 2002 June; 17(6): 1081-4) and Veronese (Veronese F V, et al. Clin Transplant. 2005 August; 19(4):518-21) found moderate to good interobserver agreement in assigning a diagnosis of acute rejection. But they did not mention whether the scores were interpreted in a centralized manner, or by each pathologist individually. In all these studies, the interobserver agreement about the conclusion drawn from the semi-quantitative criteria together with routine laboratory test results (as it is done in routine practice), has never been evaluated. Unfortunately, the vulnerability to Banff classification misinterpretation has already been demonstrated, especially for antibody-mediated rejection (Schinstock C A, et al. Am J Transplant Off J Am Soc Transplant Am Soc Transpl Surg. 2019 January; 19(1): 123-31).

Borderline TCMR cases were considered as positive TCMR in the learning and validation phases. Indeed, the aim was to propose a sensitive tool to detect rejection, considering the cost of false negative cases higher than that of false positives. Despite probably larger variability across centers for reporting borderline TCMR, consistency with the algorithm estimation was very high for these cases.

The lower and upper thresholds were chosen at 0.10 and 0.75, respectively, for both binary models: ABMR and TCMR. Indeed, the inventors observed that true negatives were distributed very closely to the score of 0, whereas the score of true positive cases were more spread out between 0.75 and 1. Furthermore, the inventors did not want to overfit the Leuven dataset.

Grading elementary lesions is not always possible, because not all biopsies are deemed adequate. The number of glomeruli and arteries visible on the slides can be very small, making it impossible to assess all criteria. More generally, in case of missing criteria, the algorithm performance might be reduced. For each classification model, the measured importance of each variable (FIG. 4) points to the critical variables. For example, diagnosing ABMR requires at least the presence of the following data: g, ptc, cg. Therefore, for routine practice, an overlay of If/Then/Else rules have been applied upstream of the current model to avoid making predictions in case one of these critical variables is missing. In contrast, the absence of any one of the minor predictors of ABMR, i.e. DSA, time after transplant, C4d staining, serum creatinine, and proteinuria, is acceptable. Another overlay was also applied for biopsies with positive BK viremia together with positive t and i criteria, so as to avoid false positive TCMR diagnostic due to BK virus nephropathy.

For future evolutions of the Banff classification, biopsies of the learning data set will be re-examined by pathologist experts and a new algorithm trained.

Finally, this study points out the imperfect reproducibility of applying the Banff rules, even in large European kidney transplantation center, and highlights the improvement artificial intelligence can bring to the interpretation of the Banff elementary lesions, to help pathologists in their routine practice, as well as minimize outcome uncertainty in multicenter clinical trials in kidney transplantation as a replacement to centralized biopsy reading.

The main limitation of this approach is that histological reading and elementary lesion grading of biopsies still depend on human skills, and variability, but the many AI tools being developed for image analysis may soon fill the gap.

CONCLUSION

In this study, the inventors built and thoroughly validated a highly sensitive and specific AI algorithm to interpret histological lesions in kidney graft biopsies, taking account of a few routine laboratory test results and clinical data. The inventors already have applied this algorithm to the 3,000+ kidney graft biopsies of a European prospective cohort study, as a replacement to centralized interpretation.

The invention claimed is:

1. A computer-implemented diagnostic method for determining active antibody-mediated rejection (ABMR) in a post-renal transplanted subject comprising the steps of:

a. collecting a set of parameters including histopathologic Banff lesion scores from 0 to 3 in a renal graft biopsy of said subject wherein said Banff lesion scores are glomerulitis (g), peritubular capillaritis (ptc) and chronic transplant glomerulopathy (cg), and b. determining by applying a trained machine-learning model on said set of parameters, whether a post-renal transplanted subject has active ABMR, wherein the collected set of parameters and on which the trained machine-learning model is applied further comprises one or more set parameter(s) selected from the group consisting of: laboratory test result determining the presence of donor-specific antibodies (DSA), clinical data determining the time between transplantation and biopsy, histopathologic Banff lesion score from 0 to 3 of C4d staining in ptc or medullary vasa recta (C4d) in a renal graft biopsy, laboratory test result determining the concentration of serum creatine and laboratory test result determining the concentration of proteinuria.

2. The method of claim 1 wherein the trained machine learning model has been trained by supervised learning on a training dataset comprising for each of a plurality of kidney biopsies, laboratory test results and clinical data of post-renal transplanted subjects, an assessment of each parameter of the set of parameters, and a clinical diagnosis of presence or absence of active ABMR provided by an expert.

3. A computer-implemented diagnostic method for determining chronic active antibody-mediated rejection (ABMR) in a post-renal transplanted subject comprising the steps of:

a. collecting a set of parameters including histopathologic Banff lesion score of chronic transplant glomerulopathy (cg) from 0 to 3 in a renal graft biopsy of said subject and clinical data determining the time between transplantation and said biopsy, and b. determining by applying a trained machine-learning model on said set of parameters whether a post-renal transplanted subject has chronic active ABMR, wherein the collected set of parameters and on which the trained machine-learning model is applied further comprises one or more set parameter(s) selected from the group consisting of: laboratory test result determining the presence of donor-specific antibodies (DSA), clinical data determining the time between transplantation and biopsy, histopathologic Banff lesion score from 0 to 3 of C4d staining in ptc or medullary vasa recta (C4d) in a renal graft biopsy, laboratory test result determining the concentration of serum creatine and laboratory test result determining the concentration of proteinuria.

4. The method of claim 3 wherein the trained machine learning model has been trained by supervised learning on a training dataset comprising for each of a plurality of kidney biopsies and clinical data of post-renal transplanted subjects, an assessment of each parameter of the set of parameters and a diagnosis of presence or absence of chronic active ABMR provided by an expert.

5. A computer-implemented diagnostic method for determining T-cell-mediated rejection (TCMR) in a post-renal transplanted subject comprising the steps of:

a. collecting a set of parameters including histopathologic Banff lesion scores from 0 to 3 of tubulitis in cortical tubules within non-scarred cortex (t) and inflammation in non-scarred cortex (i) in a renal graft biopsy of said subject, b. determining by applying a trained machine-learning model on said set of parameters, whether a post-renal transplanted subject has TCMR, wherein the collected set of parameters and on which the trained machine-learning model is applied further comprises one or more set parameter(s) selected from the group consisting of: laboratory test result determining the presence of donor-specific antibodies (DSA), clinical data determining the time between transplantation and biopsy, histopathologic Banff lesion score from 0 to 3 of C4d staining in ptc or medullary vasa recta (C4d) in a renal graft biopsy, laboratory test result determining the concentration of serum creatine and laboratory test result determining the concentration of proteinuria.

6. The method of claim 5 wherein the collected set of parameters and on which the trained machine-learning model is applied further comprises histopathologic Banff lesion score from 0 to 3 of total cortical inflammation (ti) in a renal graft biopsy.

7. The method of claim 5 wherein the trained machine learning model has been trained by supervised learning on a training dataset comprising for each of a plurality of kidney biopsies of post-renal transplanted subjects, an assessment of each parameter of the set of parameters and a clinical diagnosis of presence or absence of TCMR provided by an expert.

8. A computer-implemented diagnostic method for determining interstitial fibrosis and tubular atrophy (IFTA) in a post-renal transplanted subject comprising the steps of:

a. collecting a set of parameters including histopathologic Banff lesion scores from 0 to 3 of tubular atrophy in cortex (ct) in a renal graft biopsy of said subject, and b. determining by applying a trained machine-learning model on said set of parameters whether a post-renal transplanted subject has IFTA, wherein the collected set of parameters and on which the trained machine-learning model is applied further comprises one or more set parameter(s) selected from the group consisting of: laboratory test result determining the presence of donor-specific antibodies (DSA), clinical data determining the time between transplantation and biopsy, histopathologic Banff lesion score from 0 to 3 of C4d staining in ptc or medullary vasa recta (C4d) in a renal graft biopsy, laboratory test result determining the concentration of serum creatine and laboratory test result determining the concentration of proteinuria.

9. The method of claim 8 wherein the trained machine learning model has been trained by supervised learning on a training dataset comprising for each of a plurality of kidney biopsies of post-renal transplanted subjects, an assessment of each parameter of the set of parameters and a clinical diagnosis of presence or absence of IFTA provided by an expert.

10. The method of claim 1 further comprising a computer-implemented diagnostic method for determining chronic active antibody-mediated rejection (ABMR) in a post-renal transplanted subject comprising the steps of:

collecting a set of parameters including histopathologic Banff lesion score of chronic transplant glomerulopathy (cg) from 0 to 3 in a renal graft biopsy of said subject and clinical data determining the time between transplantation and said biopsy, and determining by applying a trained machine-learning model on said set of parameters whether a post-renal transplanted subject has chronic active ABMR.

11. A method for training a model for determining different clinical diagnoses for different combinations of transplant alterations, selected from the group consisting of: antibody-mediated rejection (ABMR), T-cell-mediated rejection (TCMR), interstitial fibrosis and tubular atrophy (IFTA), chronic ABMR or acute ABMR in a post-renal transplanted subject comprising the steps of:

a. collecting a training dataset comprising, for each of post-renal transplanted subjects:

i. a set of histopathologic Banff lesion scores from 0 to 3 in a renal graft biopsy of said subject wherein the set of Banff lesion scores comprises: glomerulitis (g), peritubular capillaritis (ptc), linear C4d staining in ptc or medullary vasa recta (C4d), chronic transplant glomerulopathy (cg), inflammation in non-scarred cortex (i), tubulitis in cortical tubules within non-scarred cortex (t), total cortical inflammation (ti), tubular atrophy in cortex (ct) and interstitial fibrosis in cortex (ci), ii. a set of laboratory test results determining the presence of donor-specific antibodies (DSA), the concentration of serum creatinine or proteinuria in the subject at the time of the biopsy or the clinical data determining time between transplantation and said biopsy, iii. an indication of the subject being subjected to at least one clinical diagnosis of renal transplant alteration among the renal transplant alteration diagnoses, b. for each clinical diagnosis of renal transplant alteration of the above-mentioned group, training a machine learning model on the training dataset, wherein the machine learning model is configured to receive as input parameters a value of each histopathologic Banff lesion score of the set of histopathologic Banff lesion scores and a value of each laboratory test result or clinical of the set of laboratory test results or clinical data, and to output an indication about whether or not the patient is suffering from a renal transplant alteration, wherein the collected set of parameters and on which the trained machine-learning model is applied further comprises one or more set parameter(s) selected from the group consisting of: laboratory test result determining the presence of donor-specific antibodies (DSA), clinical data determining the time between transplantation and biopsy, histopathologic Banff lesion score from 0 to 3 of C4d staining in ptc or medullary vasa recta (C4d) in a renal graft biopsy, laboratory test result determining the concentration of serum creatine and laboratory test result determining the concentration of proteinuria.

12. The method according to claim 11, wherein the machine learning model is a decision tree or a random forest and the training comprises performing Gradient Boosting.

13. The method according to claim 11 wherein the training dataset comprises, for at least one subject, at most one or two missing values among the set of laboratory test result, clinical data and the set of Banff lesion scores.

14. A computer program product comprising code instructions on a non-transitory computer medium for implementing the machine learning model trained by a. collecting a training dataset comprising, for each of post-renal transplanted subjects:

i. A set of histopathologic Bannflesion scores from 0 to 3 in a renal graft biopsy of said subject wherein the set of Banff lesion scores comprises: glomerulitis (g), peritubular capillaritis (ptc), linear C4d staining in ptc or medullary vasa recta (C4d), chronic transplant glomerulopathy (cg), inflammation in non-scarred cortex (i), tubulitis in cortical tubules within non-scarred cortex (t), total cortical inflammation (ti), tubular atrophy in cortex (ct) and interstitial fibrosis in cortex (ci), ii. a set of laboratory test results determining the presence of donor-specific antibodies (DSA), the concentration of serum creatinine or proteinuria in the subject at the time of the biopsy or the clinical data determining time between transplantation and said biopsy, iii. an indication of the subject being subjected to at least one clinical diagnosis of renal transplant alteration among the renal transplant alteration diagnoses, b. for each clinical diagnosis of renal transplant alteration of the above-mentioned group, training a machine learning model on the training dataset, wherein the machine learning model is configured to receive as input parameters a value of each histopathologic Banff lesion score of the set of histopathologic Banff lesion scores and a value of each laboratory test result or clinical of the set of laboratory test results or clinical data, and to output an indication about whether or not the patient is suffering from a renal transplant alteration, wherein the collected set of parameters and on which the trained machine-learning model is applied further comprises one or more set parameter(s) selected from the group consisting of: laboratory test result determining the presence of donor-specific antibodies (DSA), clinical data determining the time between transplantation and biopsy, histopathologic Banff lesion score from 0 to 3 of C4d staining in ptc or medullary vasa recta (C4d) in a renal graft biopsy, laboratory test result determining the concentration of serum creatine and laboratory test result determining the concentration of proteinuria.

15. The method of claim 4 wherein the collected set of parameters and on which the trained machine-learning model is applied further comprises interstitial fibrosis in cortex (ci) in a renal graft biopsy of said subject.

16. The method according to claim 1, further comprising a computer-implemented diagnostic method for determining T-cell-mediated rejection (TCMR) in a post-renal transplanted subject comprising the steps of:

a. collecting a set of parameters including histopathologic Banff lesion scores from 0 to 3 of tubulitis in cortical tubules within non-scarred cortex (t) and inflammation in non-scarred cortex (i) in a renal graft biopsy of said subject, and b. determining by applying a trained machine-learning model on said set of parameters, whether a post-renal transplanted subject has TCMR.

17. The method according to claim 1, further comprising a computer-implemented diagnostic method for determining interstitial fibrosis and tubular atrophy (IFTA) in a post-renal transplanted subject comprising the steps of: a. collecting a set of parameters including histopathologic Bannflesion scores from 0 to 3 of tubular atrophy in cortex (ct) in a renal graft biopsy of said subject, and b. determining by applying a trained machine-learning model on said set of parameters whether a post-renal transplanted subject has IFTA.

* * * * *